(12) United States Patent
Dittberner et al.

(10) Patent No.: US 10,924,837 B2
(45) Date of Patent: *Feb. 16, 2021

(54) ACOUSTIC DEVICE

(71) Applicant: GN HEARING A/S, Ballerup (DK)

(72) Inventors: Andrew Dittberner, Andover, MN (US); Vidya Krull, Highland Park, IL (US)

(73) Assignee: GN Hearing A/S, Ballerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/241,398

(22) Filed: Jan. 7, 2019

(65) Prior Publication Data
US 2019/0141429 A1    May 9, 2019

Related U.S. Application Data

(63) Continuation of application No. 15/673,335, filed on Aug. 9, 2017, now Pat. No. 10,212,503.

(51) Int. Cl.
| | | |
|---|---|---|
| H04R 25/00 | (2006.01) | |
| H04R 1/10 | (2006.01) | |
| H04R 5/033 | (2006.01) | |
| H04R 5/027 | (2006.01) | |
| A61F 11/14 | (2006.01) | |

(52) U.S. Cl.
CPC ............ *H04R 1/1008* (2013.01); *A61F 11/14* (2013.01); *H04R 1/1091* (2013.01); *H04R 5/027* (2013.01); *H04R 5/033* (2013.01)

(58) Field of Classification Search
CPC ..... A61F 11/14; H04R 1/1008; H04R 1/1091; H04R 5/027; H04R 5/033

USPC ........................................................ 381/370
See application file for complete search history.

(56) References Cited

U.S. PATENT DOCUMENTS

| | | | |
|---|---|---|---|
| 5,031,216 A * | 7/1991 | Gorike | H04R 5/027 |
| | | | 381/26 |
| 5,675,658 A | 10/1997 | Brittain | |
| 2005/0213774 A1 | 9/2005 | Kleinschmidt | |
| 2008/0175423 A1 | 7/2008 | Hamacher | |
| 2016/0099008 A1 | 4/2016 | Barker et al. | |
| 2019/0052946 A1* | 2/2019 | Dittberner | A61F 11/14 |

FOREIGN PATENT DOCUMENTS

| | | | | |
|---|---|---|---|---|
| DE | 25 25 642 A1 | 6/1975 | | |
| EP | 3442241 A1 * | 2/2019 | ........... | H04R 1/1091 |
| WO | WO 91/07153 A1 | 5/1991 | | |

OTHER PUBLICATIONS

European Extended Search Report dated Nov. 6, 2018 for corresponding European Application No. 18183390.6.
Notice of Allowance and Fee(s) dated Oct. 4, 2018 for related U.S. Patent Application.

* cited by examiner

*Primary Examiner* — Phylesha Dabney
(74) *Attorney, Agent, or Firm* — Vista IP Law Group, LLP

(57) ABSTRACT

A acoustic device includes a pinna replica, wherein an inner surface of the pinna replica faces the exterior so that exterior sounds are received by the pinna replica and a microphone unit for collecting said exterior sounds, said microphone unit being configured to emit a first electric signal comprising information on the collected exterior sounds.

18 Claims, 3 Drawing Sheets

ACOUSTIC DEVICE

RELATED APPLICATION DATA

This application is a continuation of U.S. patent application Ser. No. 15/673,335 filed on Aug. 9, 2017, now U.S. Pat. No. 10,212,503. The entire disclosure of the above application is expressly incorporated by reference herein.

TECHNICAL FIELD

The disclosure primarily relates to an acoustic device that improves capacity to localize sound-emitting objects in space.

BACKGROUND

As is known in the art, the faculty of hearing entails not only detection, discrimination, and comprehension of acoustic sound signals, but also the ability to localize sound-emitting objects in space.

In this context, term localization encompasses the ability to determine direction of arrival (DOA) of the acoustic sound signal as well as the distance to a sound-emitting object. As is widely known, when the ear is occluded, for instance when a hearing protection earmuff or a headphone is employed, high frequency spectral cues, present in frequencies exceeding 1500 Hz and used for perception of auditory signal depth, are lost. High frequency spectral cues or pinna-based spectral cues, along with other important cues such as interaural intensity difference (IID) and interaural level difference (ILD), contribute to improve auditory localization of sounds as well as externalization of sounds. These pinna-based spectral cues are sometimes even called the directional transfer function (DTF). The DTF forms part of the head-related transfer function (HRTF), a well-known model for representing how an ear receives a sound from a point in space.

The purpose of a pinna (auricle, outer ear) is to guide and decode incoming acoustic sound signals. When the guiding/decoding function of the pinna is disabled, it has been proposed to use signal processing in order to restore this natural filtering performed by the pinna. However, these attempts have proven inadequate. Specifically, it is currently not feasible to, in real time, identify all possible sounds, both static and dynamic, present around the listener and filter each sound based on the personalized HRTF-characteristics of the listener.

On the above background, further attempts have been made to at least alleviate drawbacks associated with the art.

A general acknowledgement of the fact that the shape of the human pinna is of importance for the ability to determine the sound direction may be found in WO91/07153. In addition, WO91/07153 proposes to shape the outer surface of the ear covering member so as to very roughly imitate the main shape of the human pinna. Further, WO91/07153 teaches that the outer, imitated pinna should be larger than the natural pinna. Such an imitated pinna improves listener's ability to determine sound direction associated with the acoustic sound signal. However, the proposed teaching is ridden with considerable drawbacks. By way of example, its accuracy in determining various auditory parameters is inherently limited by its approximative design. Further and since the employed term "sound direction" is rather general, the majority of the parameters useful for sufficiently accurately determining the position of sound-emitting objects in space are not even considered by the disclosure.

On the above background, an objective at hand is to further improve the devices belonging to the state of the art.

SUMMARY

The above stated objective is mainly achieved by means of an acoustic device according to the independent claim, and by the embodiments according to the dependent claims.

More specifically, the present disclosure provides an acoustic device comprising a supra-aural ear cup, a pinna replica at least partially enclosed by the supra-aural ear cup, wherein an inner surface of the pinna replica faces the exterior so that exterior sounds are received by the pinna replica, and a microphone unit for collecting said exterior sounds, said microphone unit being configured to emit a first electric signal comprising information on the collected exterior sounds.

In the following, positive effects and advantages of the embodiments at hand are presented with reference to the first aspect.

The solution at hand preserves the pinna-based spectral cues, i.e. personalized information generated by means of the listener's pinna. Hereby, the listener's spatial perception is substantially restored, i.e. is on the same level as if the ear wasn't occluded. More specifically, by virtue of the inventive solution that preserves cues in the high frequency region, the listener is inter alia able to perceive direction of arrival (DOA) of the sound signal, sound depth as well as proper size of auditory objects in 3D-space.

Accordingly, the individual HRTF-filtering of sound is done by the pinna replica. Filtered sound is captured by the microphone unit and will eventually be delivered to the auditory system of the listener. Here, if the computations with respect to individual HRTF-filtering are to be performed by a processing unit, a significant additional computational burden would be posed on the processing unit as these computations would need to be made substantially in real time.

The proposed embodiment(s) provides a simple, fully mechanical solution for restoring personal, pinna-based spectral cues. Consequently, such a solution is much easier to productify then a corresponding software-based solution. In the same context, the benefits of one or more embodiments described herein are basically obtained without putting to use additional signal processing resources. Obviously, this confers considerable advantages. In the related context, as the proposed solution to a large extent emulates a real-life technique, it is clearly more precise and more aurally natural than any software-based solution.

Throughout the application, the term pinna replica is to be construed as a true to life, three-dimensional reproduction of the pinna of the listener.

An acoustic device includes: a supra-aural ear cup; a pinna replica at least partially enclosed by the supra-aural ear cup, wherein an inner surface of the pinna replica faces the exterior so that exterior sounds are received by the pinna replica; and a microphone unit for collecting said exterior sounds, said microphone unit being configured to emit a first electric signal comprising information on the collected exterior sounds.

Optionally, the microphone unit is arranged at or near concha part of the pinna replica.

Optionally, in any of the above embodiments, at least the inner surface of the pinna replica is covered by acoustically transparent material.

Optionally, in any of the above embodiments, the pinna replica is manufactured using 3D-scanning and/or 3D-printing.

A headset includes the acoustic device in accordance with any of the above embodiments.

Optionally, the headset further includes a processing unit for processing the first electric signal, and a speaker unit configured to, based on the first electric signal, generate sound.

Optionally, the sound generated by the speaker unit is presented to a coupler that is hermetically sealed to ear canal of the listener.

Optionally, in any of the above embodiments, the headset is suitable for hearing protection, the hearing protection headset comprising environmental listening function.

Optionally, in any of the above embodiments, the first electric signal is additionally processed in order to compensate for the location of the pinna replica.

Optionally, in any of the above embodiments, the first electric signal is additionally processed in order to compensate for the location of the speaker unit.

An acoustic device includes: a supra-aural ear cup; a pinna replica at least partially enclosed by the supra-aural ear cup, wherein an inner surface of the pinna replica faces an exterior so that exterior sounds can be received by the pinna replica; and a microphone unit configured for receiving the exterior sounds, the microphone unit being configured to emit a first electric signal comprising information on the received exterior sounds.

Optionally, the microphone unit is arranged at or near a concha part of the pinna replica.

Optionally, at least the inner surface of the pinna replica is covered by an acoustically transparent material.

Optionally, the pinna replica is manufactured using 3D-scanning and/or 3D-printing.

A headset includes the acoustic device according to any of the above embodiments.

Optionally, the headset further includes a processing unit for processing the first electric signal, and a speaker unit configured to generate sound based on the first electric signal.

Optionally, the headset further includes a coupler that is hermetically sealed with respect to an ear canal of a user when the headset is being used by the user.

Optionally, the headset is a hearing protection headset.

Optionally, the hearing protection headset comprises an environmental listening function.

Optionally, the processing unit is further configured to process the first electric signal in order to compensate for a location of the pinna replica.

Optionally, the processing unit is further configured to process the first electric signal in order to compensate for a location of a speaker unit in the headset.

Further advantages and features of embodiments will become apparent when reading the following detailed description in conjunction with the drawings.

DETAILED DESCRIPTION

Figure 1:
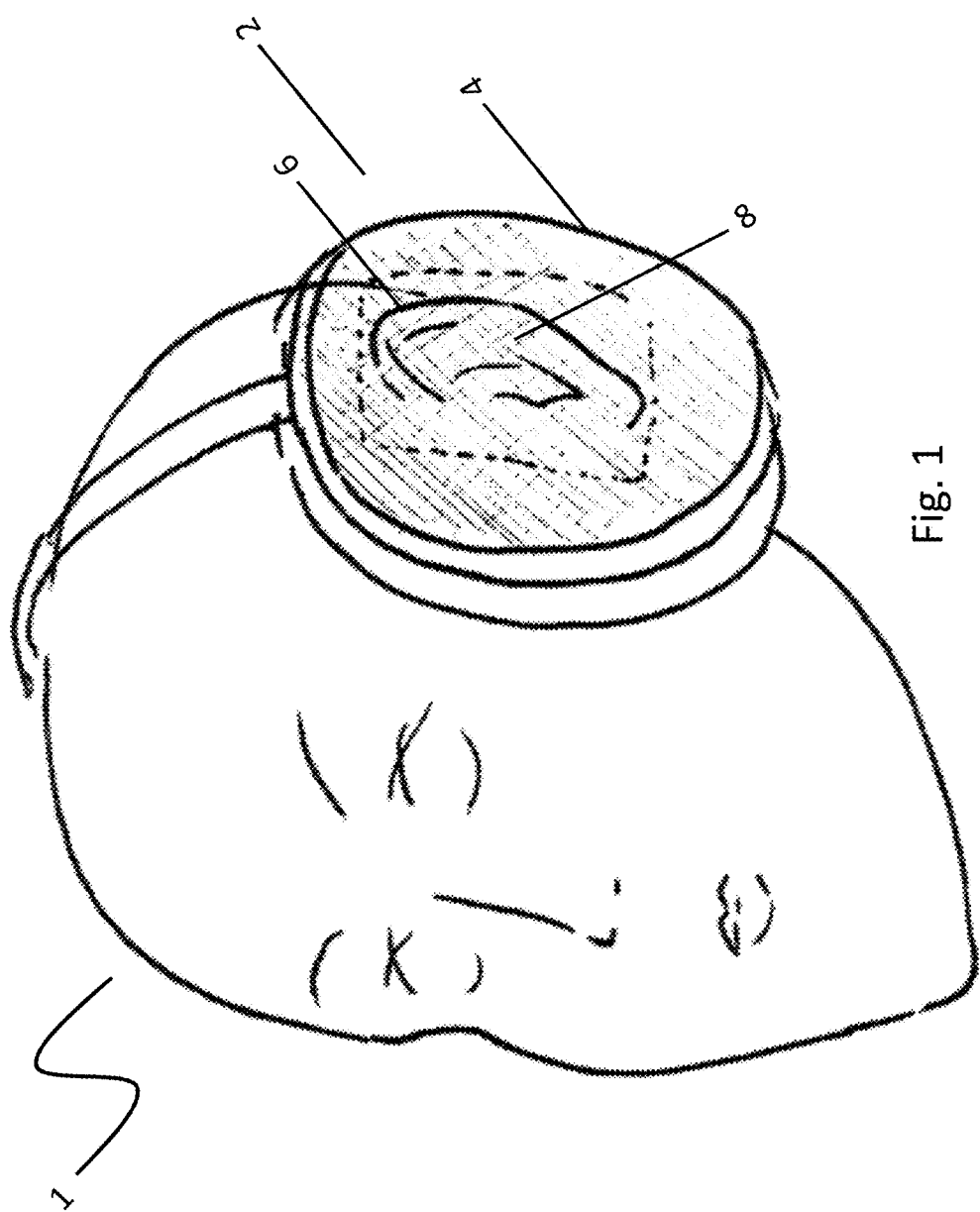
FIG. 1 is a schematic, perspective view of an acoustic device, when positioned on the ear of the listener, according to one embodiment.

The embodiments will now be described more fully hereinafter with reference to the accompanying drawings, in which exemplary embodiments are shown. It should be noted that elements of similar structures or functions are represented by like reference numerals throughout the figures. Like elements or components will therefore not necessarily be described in detail with respect to each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 is a schematic, perspective view of an acoustic device 2, when positioned on the ear of the listener 1, according to one embodiment. What is shown is an acoustic device comprising a supra-aural ear cup 4. As clearly seen, a pinna replica 6 is at least partially enclosed by the supra-aural ear cup. An inner surface 8 of the pinna replica faces the exterior. The pinna replica is arranged so that it receives the exterior sounds. A microphone unit (not shown in FIG. 1) collects said exterior sounds and emits a first electric signal comprising information on the collected exterior sounds.

Figure 2:
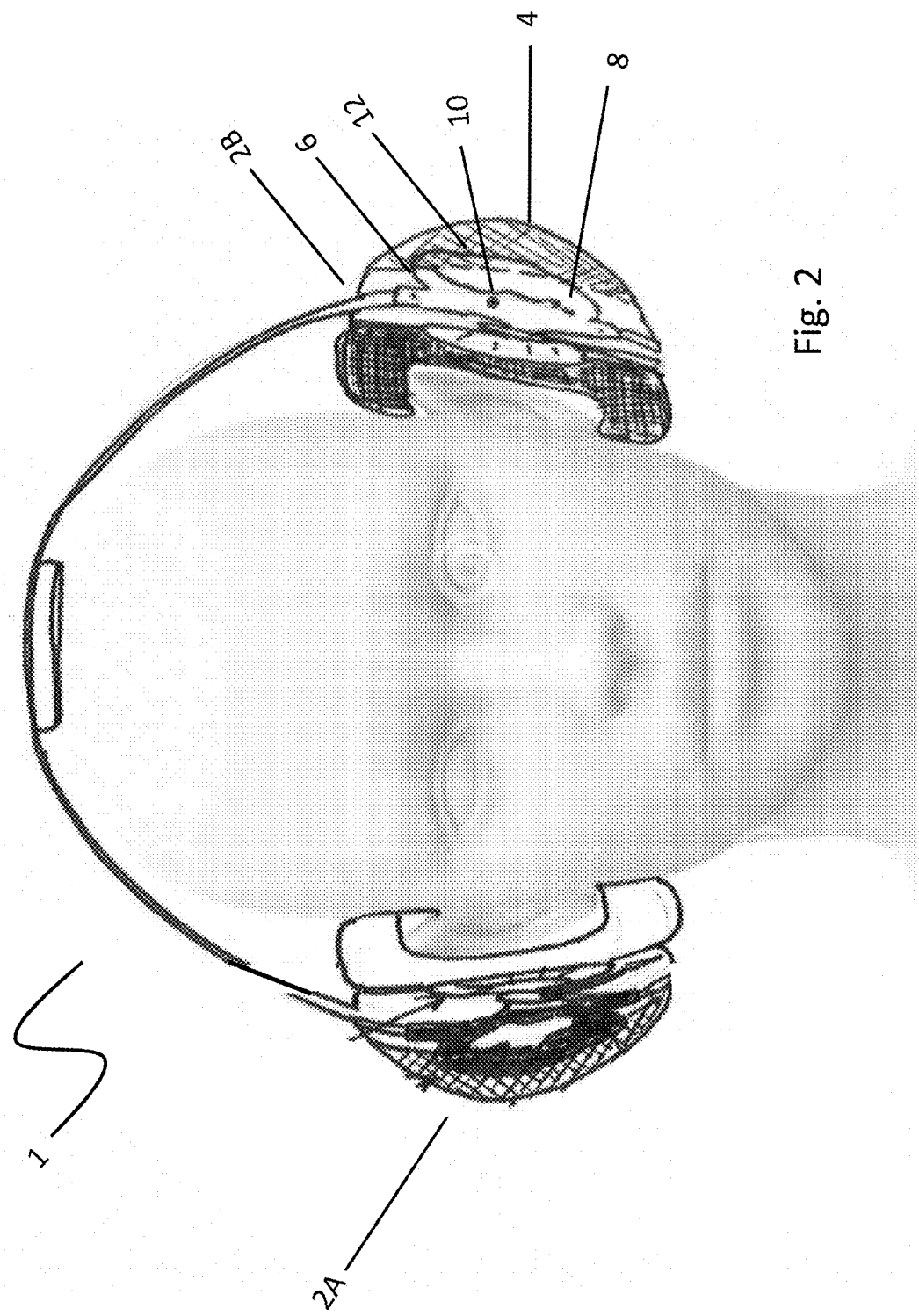
FIG. 2 is a cross-sectional front view of a pair of identical acoustic devices shown in FIG. 1, when positioned on the ear of the listener.

FIG. 2 is a cross-sectional front view of a pair of identical acoustic devices 2A, 2B shown in FIG. 1, when positioned on the ear of the listener 1. Again, an ear cup 4 and a pinna replica 6 are shown. A microphone unit 10 is also visible. For aesthetic reasons, it is desirable that the pinna replica is not visible from the exterior. This is achieved by employing acoustically transparent material 12, typically a mesh, that covers at least an inner surface 8 of the pinna replica. A further benefit conferred by this solution is a reduction of wind noise.

It is preferable to arrange the microphone unit at or near (e.g., within 1 inch, and more preferably within 0.5 inch, and more preferably within 0.3 inch, and more preferably within 0.2 inch, and more preferably within 0.1 inch, from) a concha part of the pinna replica. In this way, the sounds are captured at the entrance of the ear canal, i.e. after the natural filtering performed by the pinna has been completed.

In one embodiment, the pinna replica is manufactured using 3D-scanning and/or 3D-printing.

Figure 3:
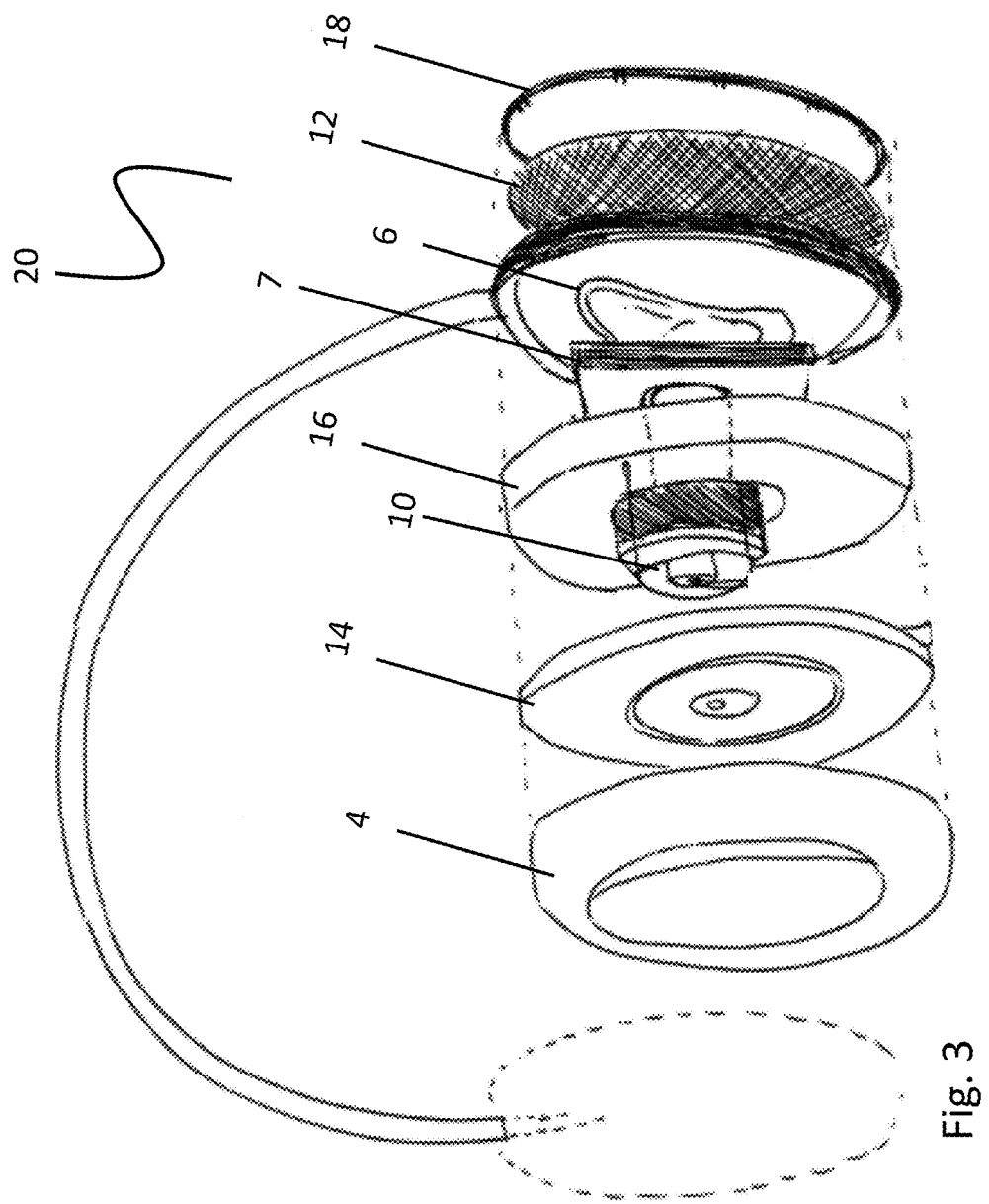
FIG. 3 is an exploded view of a headset comprising an acoustic device according to an embodiment.

FIG. 3 is an exploded view of a headset 20 comprising an acoustic device according to an embodiment. Shown acoustic device comprises a foamy, supra-aural ear cup 4 that in use rests against the listener's head, a pinna replica 6, here anchored in a base plate 7, and a microphone unit 10 for collecting exterior sounds funneled by the pinna replica.

A speaker unit 14 is arranged next to the ear cup. A coupler frame 16 including a mount with the microphone unit sits next to the speaker unit. The previously mentioned base plate with the pinna replica is arranged next to the coupler frame. In the shown embodiment, the pinna replica is covered by the previously discussed, acoustically transparent mesh 12. Further, at the outer end a ring-shaped frame 18 that provides mechanical stability is arranged.

It is to be understood that the speaker unit could be mounted in a conventional way, well-known to the artisan in the field of headsets. Alternatively, a generic ear canal coupler could be made so that the speaker unit is housed in the coupler and the coupler is attached to a headset for secure placement.

Still with reference to FIG. 3, a sound signal captured by the microphone unit of the acoustic device is typically converted to a digital signal, subsequently processed in a suitable manner by a processing unit (not shown; normally part of a headset) and finally reconverted to an analogue signal. A speaker unit (normally part of a headset) then generates the sound signal on the basis of this analogue signal.

The solution at hand preserves the pinna-based spectral cues, i.e. personalized information generated by means of the listener's pinna. Hereby, the listener's spatial perception is substantially restored, i.e. is on the same level as if the ear wasn't occluded and the pinna isn't deformed by the ear cup. More specifically, by virtue of the inventive solution that preserves cues in the high frequency region, the listener is inter alia able to perceive direction of arrival (DOA) of the sound signal, sound depth as well as proper size of auditory objects in 3D-space.

Hence, the proposed embodiment provides a simple, fully mechanical solution to preserving personal, pinna-based spectral cues. Consequently, such a solution is much easier to productify then a corresponding software-based solution. In the related context, as the proposed solution to a large extent emulates a real-life technique, it is clearly more precise and more aurally natural than any software-based solution.

As stated above, the acoustic device comprises a processing unit for suitably processing available electric signals. In this context and as argued above, by virtue of the present embodiment, the individual HRTF-filtering of sound is done by the pinna replica. Filtered sound is captured by the microphone unit and will eventually be delivered to the auditory system of the listener. Here, if the computations with respect to individual HRTF-filtering are to be performed by said processing unit, a significant additional computational burden would be posed on the processing unit as these computations would need to be made substantially in real time.

Staying in the context of the processing unit, in one embodiment the first electric signal is additionally processed in order to compensate for the location of the pinna replica. In other words, the first electric signal may undergo additional treatment in order to compensate for the fact that the filtering performed by the pinna takes place in another position in space relative the non-occluded ear. In a related embodiment, the first electric signal may undergo additional signal treatment in order to compensate for the location of the speaker unit.

The headset according to one embodiment is suitable for hearing protection. Here, such a hearing protection headset could comprise environmental listening function—a hear-through hearing protection headset.

In the drawings and specification, there have been disclosed typical preferred embodiments and, although specific terms are employed, they are used in a generic and descriptive sense only and not for purposes of limitation, the scope of the invention being set forth in the following claims.

The invention claimed is:

1. A headset comprising:
    a pinna replica, wherein the pinna replica is configured to receive exterior sound; and
    a microphone unit configured to emit a first electric signal corresponding with the exterior sound.

2. The headset according to claim 1, wherein the microphone unit is arranged at or near a concha part of the pinna replica.

3. The headset according to claim 1, wherein at least a part of the pinna replica is covered by an acoustically transparent material.

4. The headset according to claim 1, wherein the pinna replica is manufactured using 3D-scanning and/or 3D-printing.

5. The headset according to claim 1, further comprising a processing unit for processing the first electric signal, and a speaker unit configured to generate sound based on the first electric signal.

6. The headset according to claim 5, further comprising a coupler that is hermetically sealed with respect to an ear canal of a user when the headset is being used by the user.

7. The headset according to claim 5, wherein the processing unit is further configured to process the first electric signal in order to compensate for a location of the pinna replica.

8. The headset according to claim 5, wherein the processing unit is further configured to process the first electric signal in order to compensate for a location of a speaker unit in the headset.

9. The headset according to claim 1, wherein the headset is a hearing protection headset.

10. The headset according to claim 9, wherein the hearing protection headset comprises an environmental listening function.

11. An acoustic device comprising:
    a pinna replica, wherein the pinna replica is configured to receive exterior sound; and
    a microphone unit configured to emit a first electric signal corresponding with the exterior sound;
    wherein the acoustic device is configured to form a part of a headset.

12. The acoustic device according to claim 11, wherein the microphone unit is arranged at or near a concha part of the pinna replica.

13. The acoustic device according to claim 11, wherein at least a part of the pinna replica is covered by an acoustically transparent material.

14. The acoustic device according to claim 11, wherein the pinna replica is manufactured using 3D-scanning and/or 3D-printing.

15. The acoustic device according to claim 11, further comprising a processing unit for processing the first electric signal, and a speaker unit configured to generate sound based on the first electric signal.

16. The acoustic device according to claim 15, wherein the processing unit is further configured to process the first electric signal in order to compensate for a location of the pinna replica.

17. The acoustic device according to claim 15, wherein the processing unit is further configured to process the first electric signal in order to compensate for a location of a speaker unit in the headset.

18. The acoustic device according to claim 11, further comprising a coupler that is configured to form a seal with respect to an ear canal of a user.

* * * * *